US010636577B2

(12) United States Patent
Bakshi et al.

(10) Patent No.: US 10,636,577 B2
(45) Date of Patent: Apr. 28, 2020

(54) SAFE HANDLING OF LINK ERRORS IN A PERIPHERAL COMPONENT INTERCONNECT EXPRESS (PCIE) DEVICE

(71) Applicant: QUALCOMM Incorporated, San Diego, CA (US)

(72) Inventors: William Bakshi, Ramat Gan (IL); Nabeel Achlaug, Kfar Kama (IL)

(73) Assignee: Qualcomm Incorporated, San Diego, CA (US)

( * ) Notice: Subject to any disclaimer, the term of this patent is extended or adjusted under 35 U.S.C. 154(b) by 224 days.

(21) Appl. No.: 15/989,306

(22) Filed: May 25, 2018

(65) Prior Publication Data

US 2019/0361763 A1    Nov. 28, 2019

(51) Int. Cl.

| G06F 11/00 | (2006.01) |
|---|---|
| H01G 9/052 | (2006.01) |
| H01G 9/10 | (2006.01) |
| H01G 9/145 | (2006.01) |
| H01G 9/02 | (2006.01) |
| H01G 9/008 | (2006.01) |
| H01G 9/28 | (2006.01) |
| H01G 9/00 | (2006.01) |
| A61N 1/39 | (2006.01) |
| H01G 9/028 | (2006.01) |
| H01G 9/06 | (2006.01) |
| H01G 9/15 | (2006.01) |
| A61N 1/378 | (2006.01) |
| H01G 9/04 | (2006.01) |

(52) U.S. Cl.
CPC ............ *H01G 9/052* (2013.01); *A61N 1/378* (2013.01); *A61N 1/3975* (2013.01); *H01G 9/008* (2013.01); *H01G 9/0029* (2013.01); *H01G 9/02* (2013.01); *H01G 9/028* (2013.01); *H01G 9/06* (2013.01); *H01G 9/10* (2013.01); *H01G 9/145* (2013.01); *H01G 9/15* (2013.01); *H01G 9/28* (2013.01); *H01G 2009/05* (2013.01)

(58) Field of Classification Search
CPC ............ G06F 11/0745; G06F 11/0793; G06F 11/3051; G06F 2213/0026; G06F 13/4221
See application file for complete search history.

(56) References Cited

U.S. PATENT DOCUMENTS 8,402,320 B2   3/2013  Watkins et al.
9,195,552 B2   11/2015 Shao et al.
(Continued)

*Primary Examiner* — Joshua P Lottich
(74) *Attorney, Agent, or Firm* — Withrow & Terranova, PLLC

(57) ABSTRACT

Safe handling of link errors in a Peripheral Component Interconnect (PCI) express (PCIE) device is disclosed. In one aspect, safe handling of link errors involves detecting errors in a PCIE link and maintaining the PCIE link by preventing the reporting of detected errors and providing safe data to a host in communication with the PCIE link. A PCIE link can be established between a host (incorporating a root complex) and an endpoint device, through which the host can request the performance of operations (e.g., read data, write data) by the endpoint device. Circuitry and/or software can monitor the PCIE link and perform safe handling of link errors when they occur. The circuitry detects link errors and consumes them in such a manner that the host is unaware that an error has occurred and only safe (e.g., non-corrupted) data is provided to the host.

30 Claims, 11 Drawing Sheets

(56) References Cited

U.S. PATENT DOCUMENTS

| | | |
|---|---|---|
| 9,244,874 B2 | 1/2016 | Hearn et al. |
| 9,262,270 B2 | 2/2016 | Jayaprakash Bharadwaj et al. |
| 9,262,363 B2 | 2/2016 | Luo et al. |
| 9,892,078 B2 | 2/2018 | Wakuda |
| 10,229,017 B1* | 3/2019 | Zou .................... G06F 11/2007 |
| 2003/0023932 A1* | 1/2003 | Arndt ................. G06F 11/0712 |
| | | 714/805 |
| 2012/0079312 A1* | 3/2012 | Muthrasanallur ... G06F 11/0745 |
| | | 714/5.1 |
| 2013/0007507 A1* | 1/2013 | Raj .................... G06F 11/0715 |
| | | 714/5.11 |
| 2015/0143175 A1* | 5/2015 | Kidamura ........... G06F 11/0793 |
| | | 714/23 |
| 2016/0224442 A1* | 8/2016 | Sanghi ................ G06F 13/4022 |
| 2017/0337069 A1 | 11/2017 | Huang et al. |

\* cited by examiner

SAFE HANDLING OF LINK ERRORS IN A PERIPHERAL COMPONENT INTERCONNECT EXPRESS (PCIE) DEVICE

BACKGROUND

I. Field of the Disclosure

The technology of the disclosure relates generally to error management on a bus, and more particularly to error management on a Peripheral Component Interconnect express (PCIE) bus.

II. Background

Mobile communication devices have become increasingly common in current society. The prevalence of these mobile communication devices is driven in part by the many functions that are now enabled on such devices. Increased processing capabilities in such devices means that mobile communication devices have evolved from pure communication tools into sophisticated mobile multimedia centers that enable enhanced user experiences. Such increased functionality is enabled by the inclusion of evermore complex integrated circuits (ICs) within mobile communication devices. As the number and complexity of ICs within mobile communication devices has increased, so has the need for the various ICs to communicate with one another.

Various internal buses may be used to exchange data between the ICs, such as Inter-integrated circuit (I2C), serial AT attachment (SATA), serial peripheral interface (SPI), or other serial interfaces. One popular bus is based on the Peripheral Component Interconnect (PCI) express (PCIE) standard published by the PCI Special Interest Group (PCI-SIG). PCIE is a high-speed point-to-point serial bus. PCIE version 4 was officially announced on Jun. 8, 2017, and version 5 has been preliminary proposed at least as early as June 2017 with expected release in 2019. In this regard, a PCIE system includes a root complex and one or more PCIE endpoints. The root complex denotes the root of an input/output (I/O) hierarchy that connects a central processing unit (CPU) and/or a memory to the PCIE endpoints over one or more PCIE links. As such, the root complex is functionally equivalent to a router in the PCIE system to route peer-to-peer transactions between the CPU, the memory, and the PCIE endpoints.

Errors can occur in the PCIE links and/or the PCIE endpoints of the PCIE system. Some errors can be considered correctable errors, where there may be an impact on performance (e.g., latency, bandwidth) of a PCIE link, but no data is lost and the PCIE link remains reliable. Correctable errors may be corrected by PCIE hardware. Uncorrectable errors can result in lost information and/or impact the integrity of the PCIE link. Generally, uncorrectable errors cannot be corrected by PCIE hardware, and typically result in crashes of drivers and/or portions of operating systems in communication with the root complex. As a consequence, when an uncorrectable error is detected by the root complex, the PCIE link is generally terminated and re-established to prevent crashes and other disruptions from occurring.

SUMMARY OF THE DISCLOSURE

Aspects disclosed in the detailed description include safe handling of link errors in a Peripheral Component Interconnect (PCI) express (PCIE) device. In this regard, safe handling of link errors involves detecting errors in a PCIE link and maintaining the PCIE link by preventing the reporting of detected errors and providing safe data to a host in communication with the PCIE link. A PCIE link can be established between a host device (incorporating a root complex) and an endpoint device, through which the host device can request the performance of operations (e.g., read data, write data) by the endpoint device. Circuitry (e.g., safe error circuitry or control circuitry) and/or software can monitor the PCIE link and perform safe handling of link errors when they occur. The circuitry detects link errors and consumes them in such a manner that at least a portion of the host device is unaware that an error has occurred and only safe (e.g., non-corrupted) data is provided to the host device. Accordingly, the host device will not experience a crash or need to re-establish (e.g., reset) the PCIE link, during which time the PCIE link may be recovered and unaffected processes can continue to operate.

In a first non-limiting example, safe handling of link errors can be implemented on a host device, through control circuitry coupled to the root complex and/or software, such as driver software for the PCIE link. In a second non-limiting example, safe handling of link errors can be implemented on a bridge between a host device and an endpoint device, through control circuitry which can be semi-transparent to the host device. In a third non-limiting example, safe handling of link errors can be implemented on an endpoint device, through control circuitry which monitors error conditions and consumes errors before they would be reported at the PCIE link.

In this regard in one aspect, a PCIE root complex device is provided. The PCIE root complex device includes a bus interface configured to be coupled to a PCIE endpoint. The PCIE root complex device also includes control circuitry configured to establish a PCIE link between the PCIE root complex device and the PCIE endpoint over the bus interface, send an operation request to the PCIE endpoint through the PCIE link, detect an error in the PCIE link, and consume the error to avoid re-establishing the PCIE link. Consuming the error includes reporting to a host of the PCIE root complex device that no error occurred and providing safe data to the host in response to the operation request.

In another aspect, a semi-transparent bridge for a PCIE link is provided. The semi-transparent bridge includes a first bus interface configured to couple to a PCIE endpoint and a second bus interface configured to couple to a PCIE root complex. The semi-transparent bridge also includes control circuitry configured to forward an operation request from the second bus interface to the first bus interface, monitor the first bus interface for a link error, and consume the link error. Consuming the link error includes reporting to the second bus interface that no link error occurred and providing safe data to the second bus interface in response to the operation request.

In another aspect, a method is provided. The method includes establishing a PCIE link between an originator and an endpoint and receiving an operation request from the originator to the endpoint. The method also includes detecting an error in the PCIE link and consuming the error to avoid re-establishing the PCIE link. Consuming the error includes reporting to the originator that no error occurred and providing safe data to the originator in response to the operation request.

In another aspect, a system is provided. The system includes a PCIE root complex device, which includes a first PCIE bus interface to be coupled to a PCIE link and first control circuitry configured to send an operation request over the PCIE link via the first PCIE bus interface. The system also includes a PCIE endpoint device, which includes a second PCIE bus interface to be coupled to the PCIE link and second control circuitry configured to receive the operation request via the second PCIE bus interface and process the operation request. The system also includes safe error circuitry configured to detect an error in the PCIE link and consume the error, by reporting to a host in the PCIE root complex device that no error occurred in the PCIE link and providing safe data to the host in response to the operation request.

DETAILED DESCRIPTION

Figure 1:
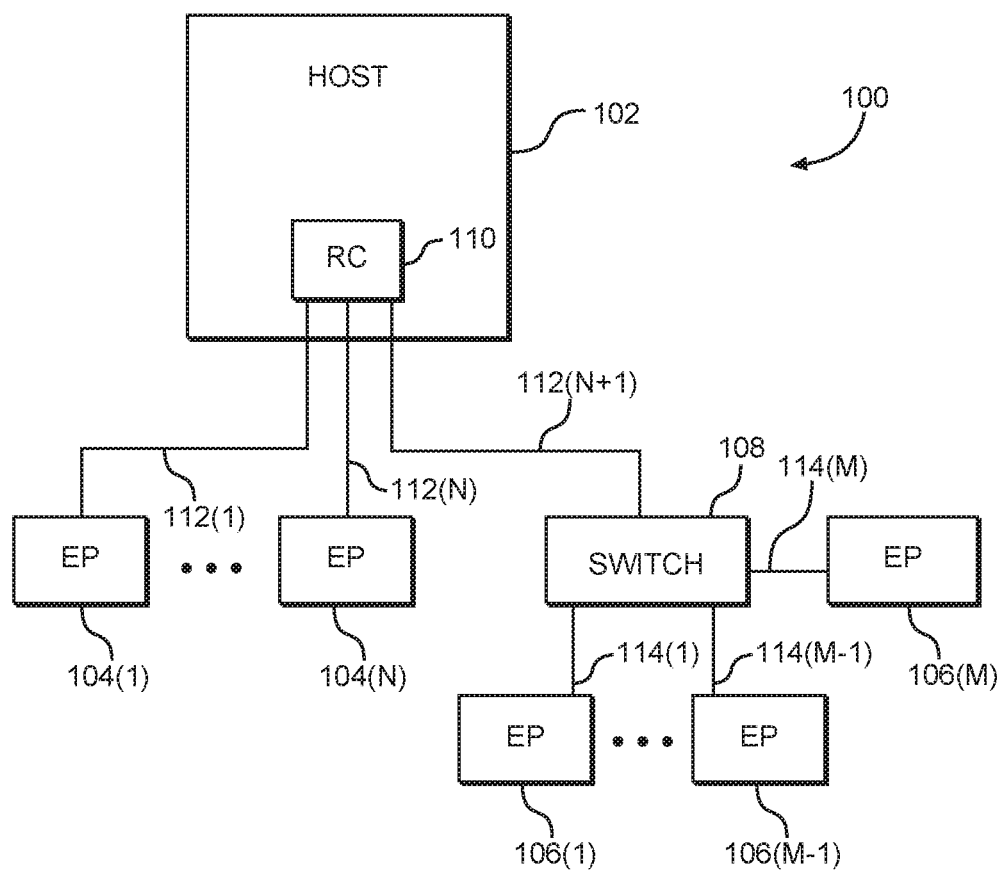
FIG. 1 is a block diagram of an exemplary computing system with devices coupled by Peripheral Component Interconnect (PCI) express (PCIE) buses.

With reference now to the drawing figures, several exemplary aspects of the present disclosure are described. The word "exemplary" is used herein to mean "serving as an example, instance, or illustration." Any aspect described herein as "exemplary" is not necessarily to be construed as preferred or advantageous over other aspects.

Aspects disclosed in the detailed description include safe handling of link errors in a Peripheral Component Interconnect (PCI) express (PCIE) device. In this regard, safe handling of link errors involves detecting errors in a PCIE link and maintaining the PCIE link by preventing the reporting of detected errors and providing safe data to a host in communication with the PCIE link. A PCIE link can be established between a host device (incorporating a root complex) and an endpoint device, through which the host device can request the performance of operations (e.g., read data, write data) by the endpoint device. Circuitry (e.g., safe error circuitry or control circuitry) and/or software can monitor the PCIE link and perform safe handling of link errors when they occur. The circuitry detects link errors and consumes them in such a manner that at least a portion of the host device is unaware that an error has occurred and only safe (e.g., non-corrupted) data is provided to the host device. Accordingly, the host device will not experience a crash or need to re-establish (e.g., reset) the PCIE link, during which time the PCIE link may be recovered and unaffected processes can continue to operate.

In a first non-limiting example, safe handling of link errors can be implemented on a host device, through control circuitry coupled to the root complex and/or software, such as driver software for the PCIE link. In a second non-limiting example, safe handling of link errors can be implemented on a bridge between a host device and an endpoint device, through control circuitry which can be semi-transparent to the host device. In a third non-limiting example, safe handling of link errors can be implemented on an endpoint device, through control circuitry which monitors error conditions and consumes errors before they would be reported at the PCIE link.

Figure 2:
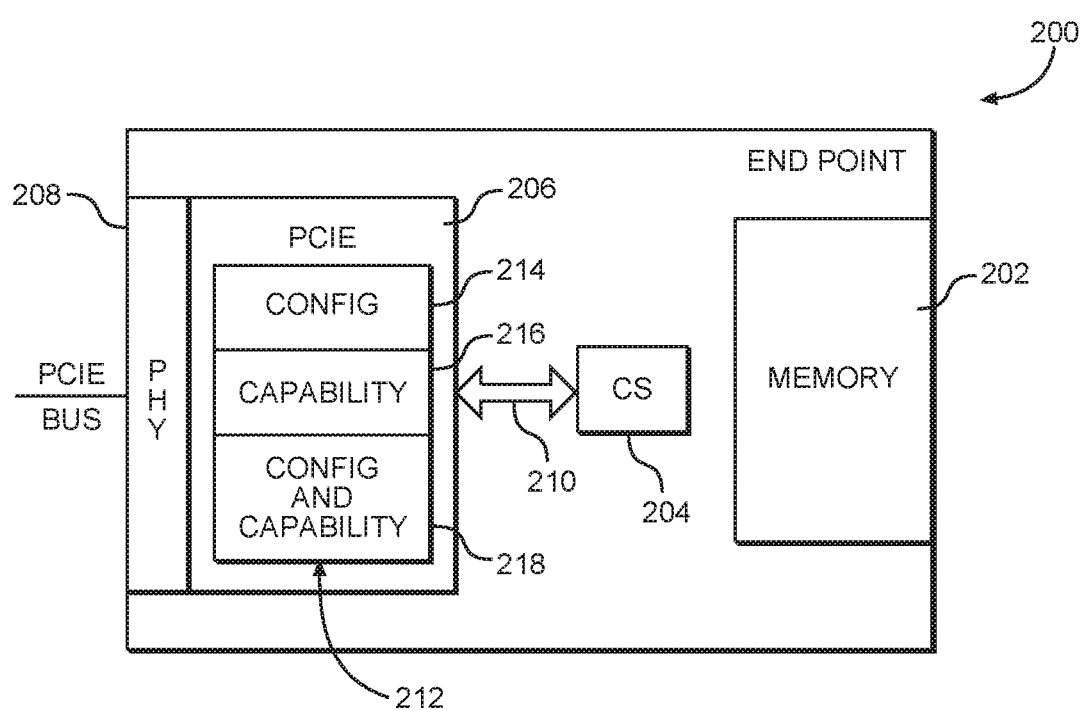
FIG. 2 is a block diagram of an exemplary PCIE endpoint device and, particularly, configuration registers within the endpoint.
Figure 3:
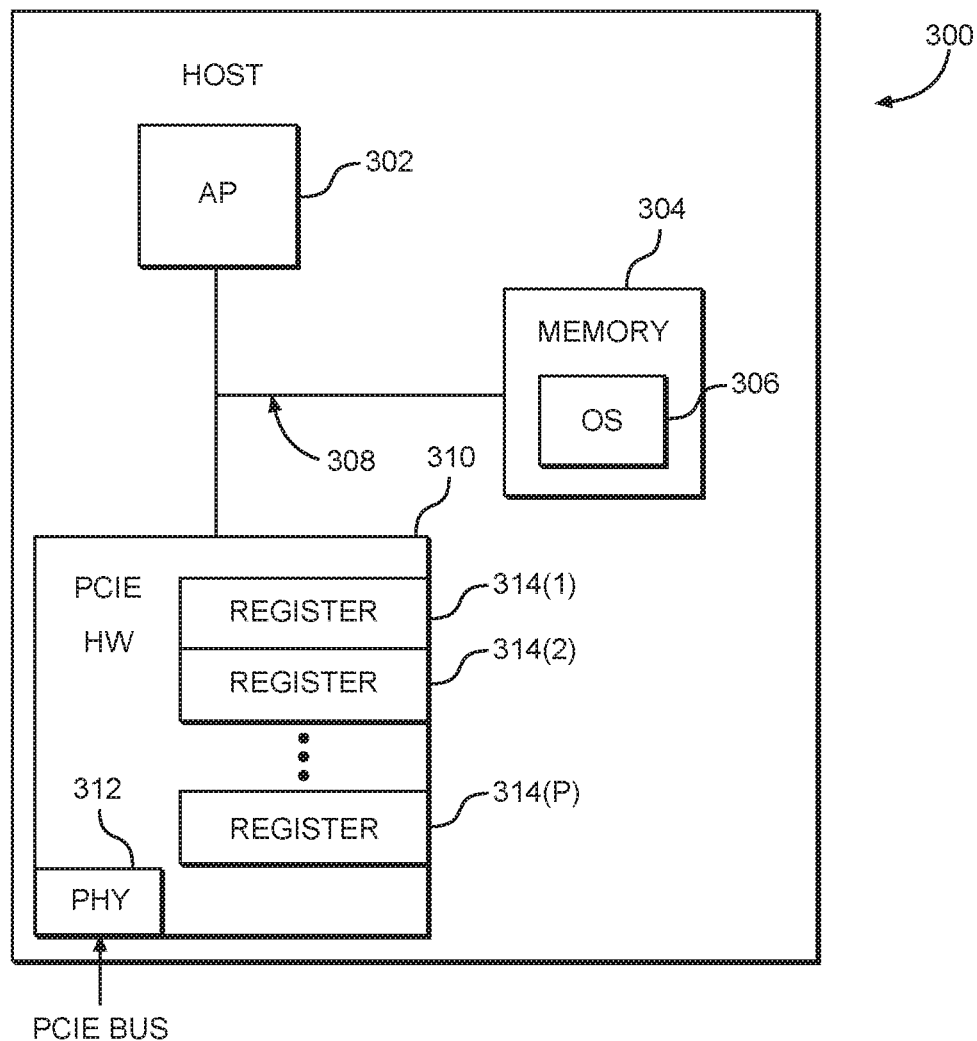
FIG. 3 is a block diagram of an exemplary host having a processor and PCIE hardware with registers according to an exemplary aspect of the present disclosure.
Figure 4A:
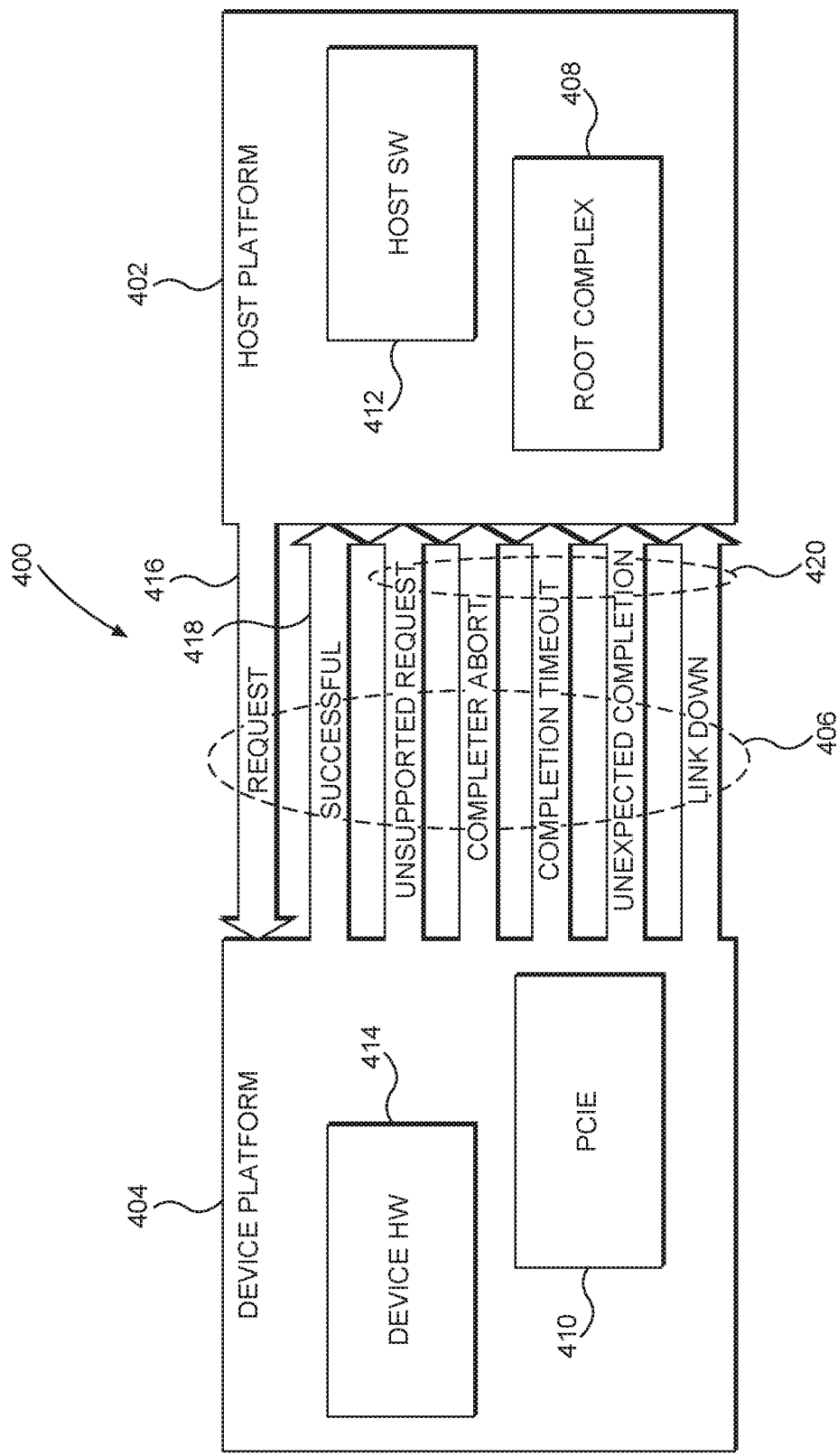
FIG. 4A is a block diagram of an exemplary computing system with a host platform and a device platform coupled by a PCIE bus.
Figure 4B:
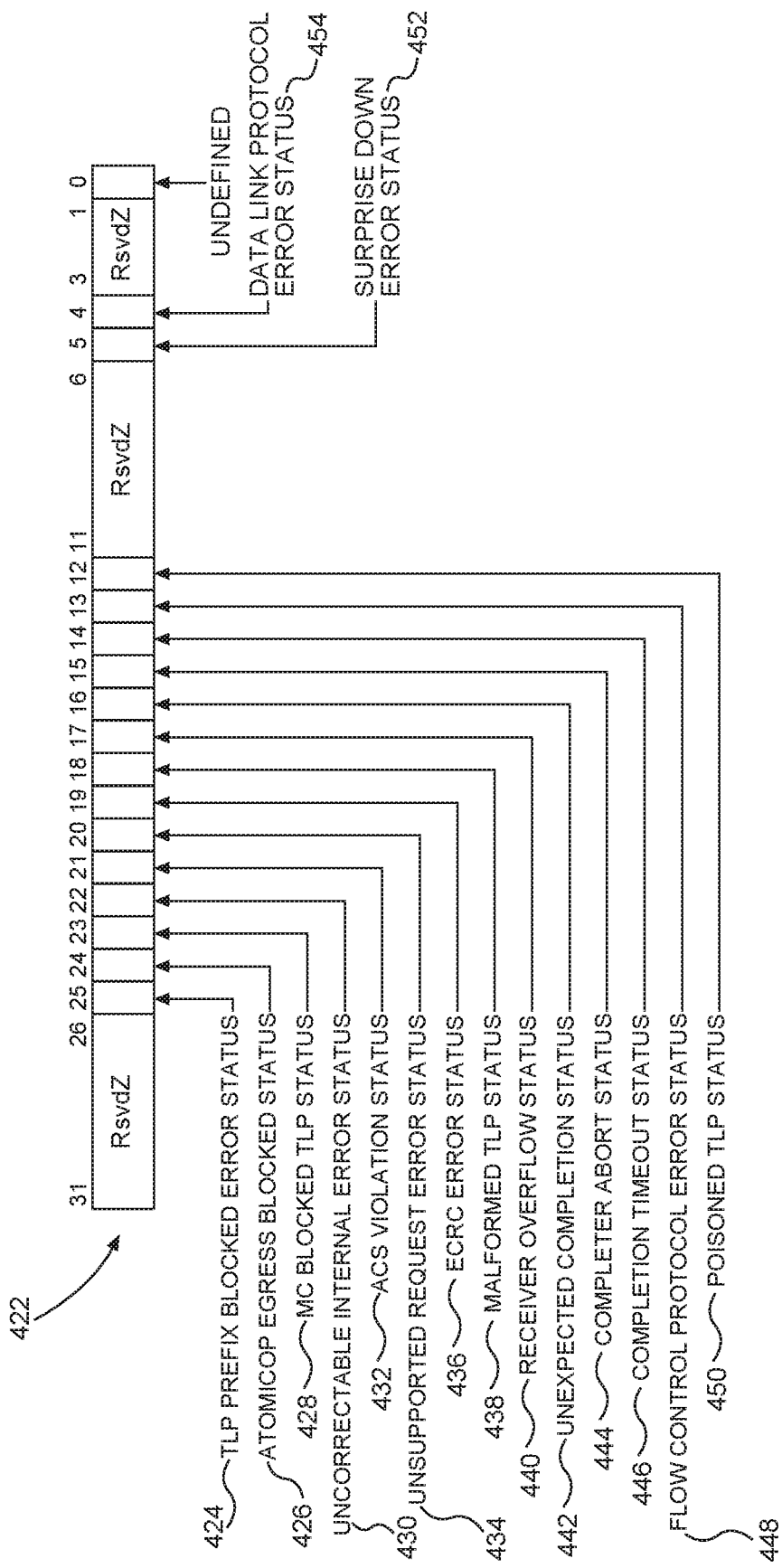
FIG. 4B is a block diagram of an exemplary PCIE uncorrectable error register.
Figure 5:
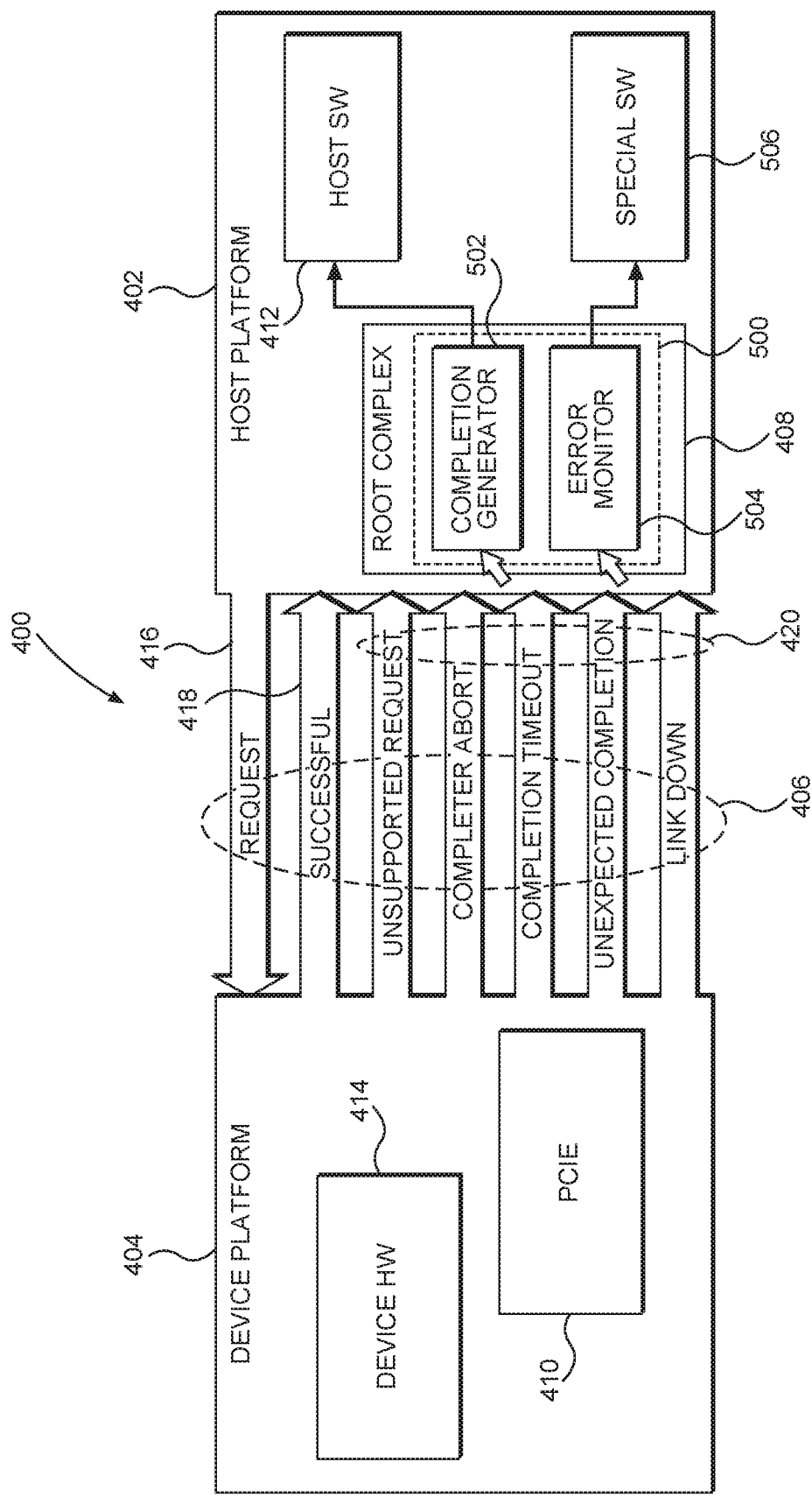
FIG. 5 is a block diagram of the exemplary computing system of FIG. 4A with the host platform incorporating safe error circuitry and/or software.
Figure 6:
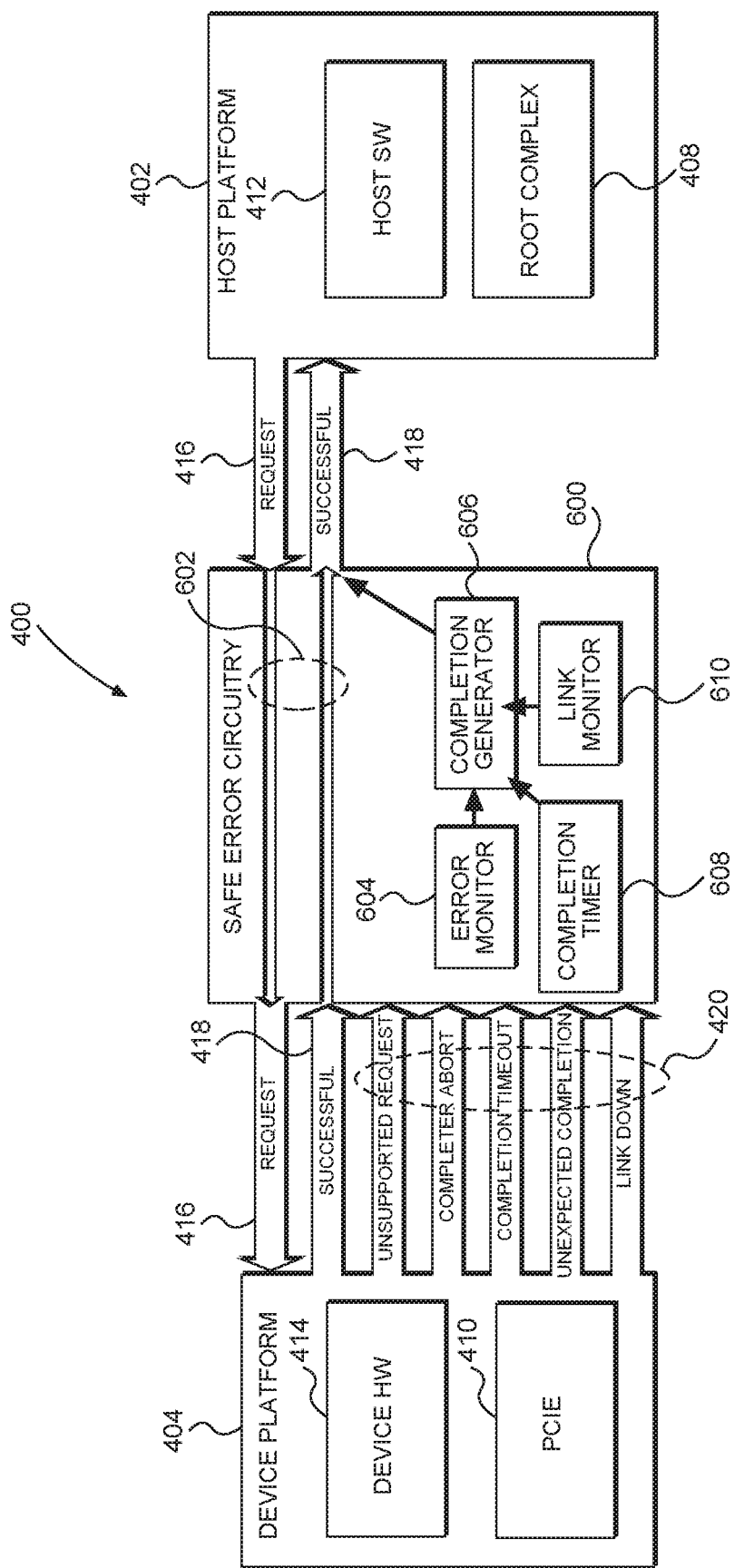
FIG. 6 is a block diagram of the exemplary computing system of FIG. 4A with a bridge between the host platform and the device platform incorporating safe error circuitry.
Figure 7:
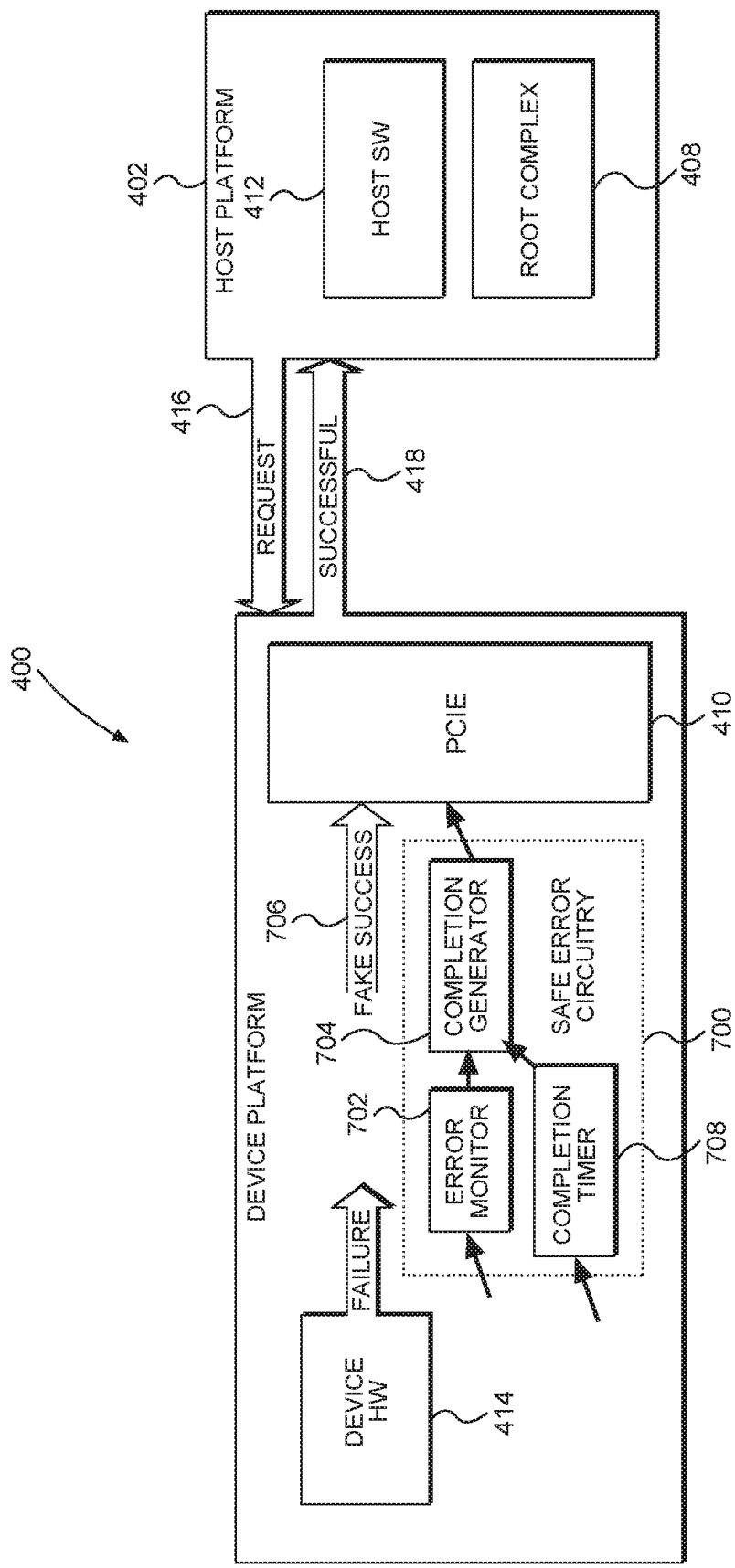
FIG. 7 is a block diagram of the exemplary computing system of FIG. 4A with the device platform incorporating safe error circuitry.
Figure 9:
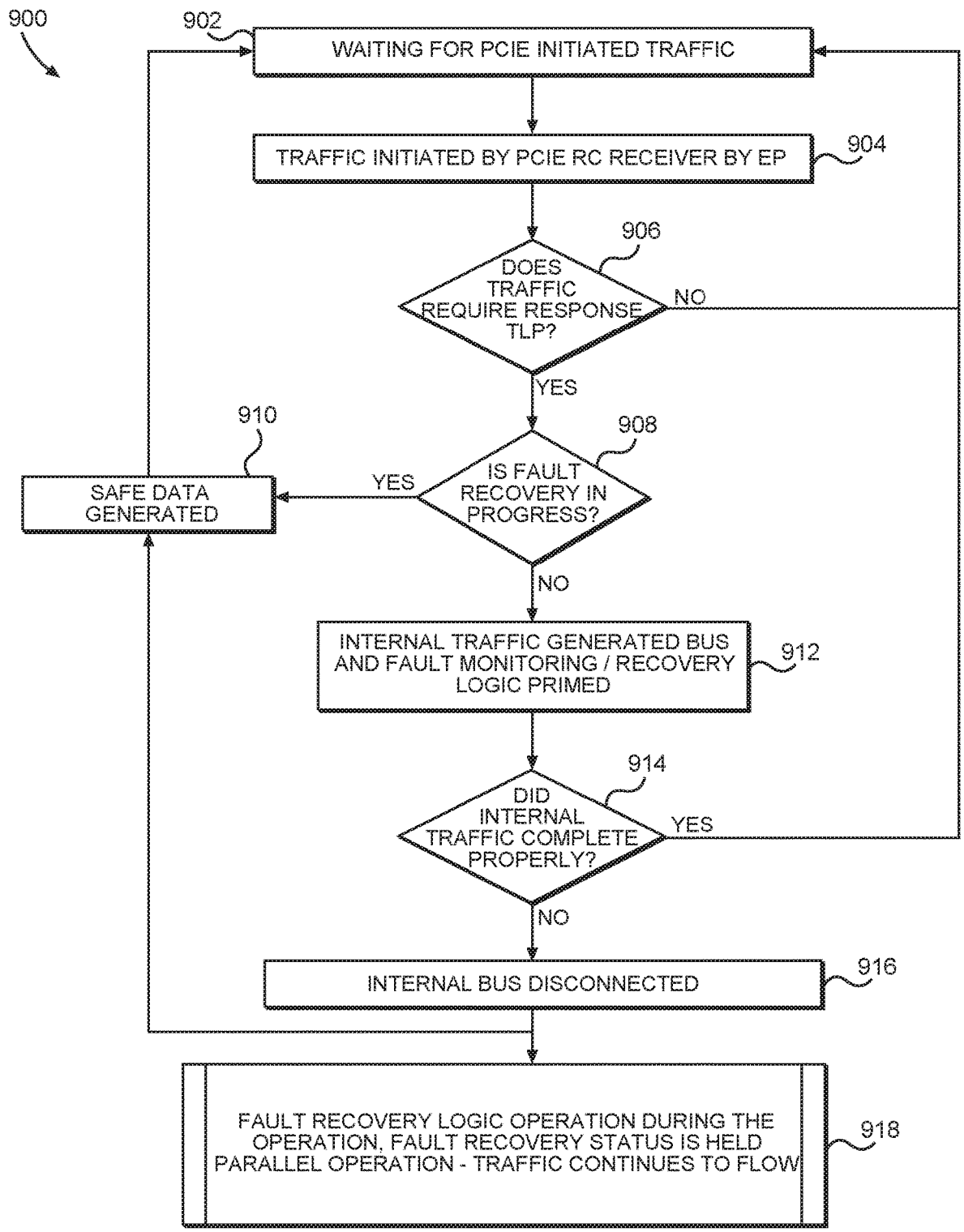
FIG. 9 is a flowchart illustrating an exemplary process for safe handling of link errors in the PCIE computing system depicted in FIGS. 4A, 4B, and 7.
Figure 10:
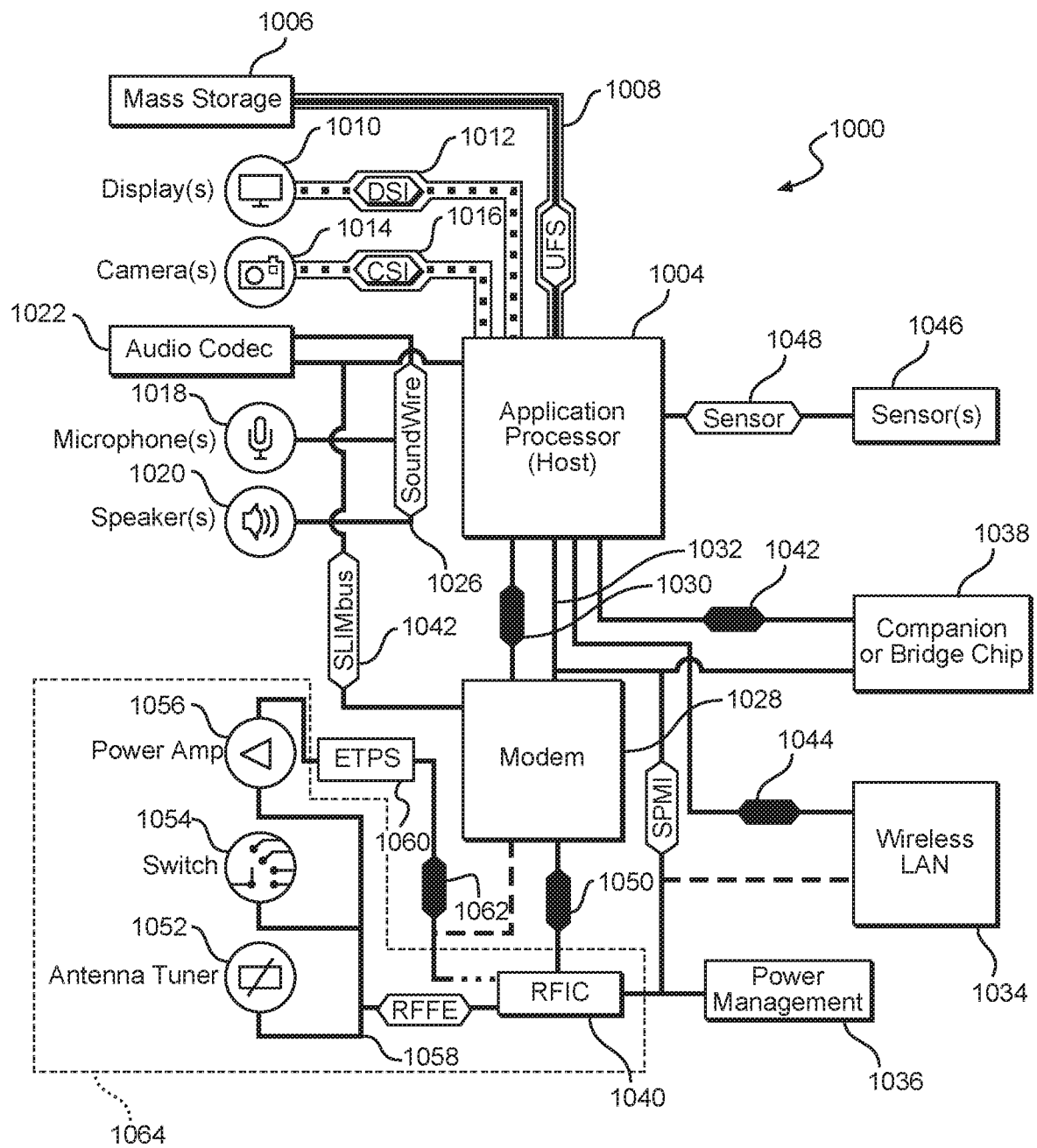
FIG. 10 is a block diagram of an exemplary processor-based system that can include the computing system of FIGS. 1-9.

To assist in understanding aspects of the present disclosure, an overview of a PCIE environment is provided with reference to FIGS. 1-3. An exemplary computing system with a host platform and device platform coupled by a PCIE bus that may include safe error circuitry and/or software is illustrated in FIG. 4A. An exemplary uncorrectable error status register, which may store and/or report an indication an error has occurred is illustrated in FIG. 4B. Exemplary implementations of safe error circuitry and/or software are illustrated in FIGS. 5-7. Exemplary processes for safe handling of link error are discussed with reference to FIGS. 8 and 9. An exemplary processor-based system that incorporates safe error handling is illustrated in FIG. 10.

In this regard, FIG. 1 illustrates a computing environment 100 with a host 102 coupled to a first plurality of devices 104(1)-104(N) directly and to a second plurality of devices 106(1)-106(M) through a switch 108. The host 102 may include a PCIE root complex 110 that includes a bus interface (not illustrated directly) that is configured to couple to plural PCIE buses 112(1)-112(N+1). The switch 108 enables the host 102 to communicate with the devices 106(1)-106(M) through additional PCIE buses 114(1)-114(M). The devices 104(1)-104(N) and 106(1)-106(M) may be or may include PCIE endpoints. In a first exemplary aspect, the computing environment 100 may be a single computing device such as a computer with the host 102 being a central processing unit (CPU) and the devices 104(1)-104(N) and 106(1)-106(M) being internal components such as hard drives, disk drives, or the like. In a second exemplary aspect, the computing environment 100 may be a computing device where the host 102 is an integrated circuit (IC) on a board and the devices 104(1)-104(N) and 106(1)-106(M) are other ICs within the computing device. In a third exemplary aspect, the computing environment 100 may be a computing device having an internal host 102 coupled to external devices 104(1)-104(N) and 106(1)-106(M) such as a server coupled to one or more external memory drives. Note that these aspects are not necessarily mutually exclusive in that different ones of the devices may be ICs, internal, or external relative to a single host 102.

FIG. 2 provides a block diagram of a device 200 that may be one of the devices 104(1)-104(N) or the devices 106(1)-106(M). In particular, the device 200 acts as an endpoint in a PCIE system, and may be, for example, a memory device that includes a memory element 202 and a control system 204. Further, the device 200 includes a PCIE hardware element 206 that includes a bus interface configured to couple to a PCIE bus. The PCIE hardware element 206 may include a physical layer (PHY) 208 that is, or works with, the bus interface to communicate over the PCIE bus. The control system 204 communicates with the PCIE hardware element 206 through a system bus 210. The PCIE hardware element 206 may further include a plurality of registers 212. The registers 212 may be conceptually separated into configuration registers 214 and capability registers 216. The configuration registers 214 and the capability registers 216 are defined by the original PCI standard, and more recent devices that include the registers 214 and 216 are backward compatible with legacy devices. The configuration registers 214 include sixteen (16) double words (DWs). The capability registers 216 include forty-eight (48) DWs. The PCIE standard further defines additional registers found in a PCIE extended configuration register space 218. These registers did not exist in the original PCI standard, and thus, PCI legacy devices generally do not address these extra registers. The PCIE extended configuration register space 218 may be another 960 DWs.

Similarly, FIG. 3 illustrates a host 300 which may be the host 102 of FIG. 1. The host 300 may include an application processor 302 or other processor core which communicates with a memory element 304 having an operating system 306 operating therewith. A system bus 308 interconnects the application processor 302 with the memory element 304 and a PCIE root complex 310. The PCIE root complex 310 may include a PHY 312 that works with or is a bus interface configured to couple to a PCIE bus. The PCIE root complex 310 can further include one or more registers 314(1)-314(P) to enable aspects of the present disclosure.

FIG. 4A is a block diagram of an exemplary computing system 400 with a host platform 402 and a device platform 404 coupled by a PCIE bus 406. The computing system 400 may be or include the computing environment 100 depicted in FIG. 1, the device platform 404 may be or include the device 200 in FIG. 2, and the host platform 402 may be or include the host 300 in FIG. 3. In this regard, the host platform 402 includes a PCIE root complex 408 that includes a bus interface (not illustrated directly) that is configured to couple to the device platform 404 via the PCIE bus 406. Similarly, the device platform 404 includes a PCIE hardware element 410 that includes a bus interface (not illustrated directly) that is configured to couple to the host platform 402 via the PCIE bus 406.

The exemplary computing system 400 includes circuitry and/or software to safely handle errors in the PCIE link between the root complex 408 of the host platform 402 and the PCIE hardware element 410 in the device platform 404 (e.g., a PCIE endpoint). In this regard, safe handling of link errors involves detecting errors in the PCIE link and maintaining the PCIE link by preventing the reporting of detected errors and providing safe data to the host platform 402 and/or host software 412 (e.g., an operating system).

In an exemplary aspect, once the PCIE link is established between the host platform 402 and the device platform 404, an originator, such as the host software 412, can cause the root complex 408 to send one or more operation requests 416 (e.g., a read request, a write request) to the PCIE hardware element 410 over the PCIE bus 406. If the operation is successful, successful data 418 and/or a report indicating success is sent from the PCIE hardware element 410 to the root complex 408 over the PCIE bus 406. However, in some cases an error can occur in the PCIE link and/or the device platform 404 (e.g., an error may occur and/or be reported by hardware in the device platform 404).

Certain errors in the PCIE link can impact the integrity of the PCIE link, and may cause disruptions in the host software 412 and/or the root complex 408. These errors are generally reported to the root complex 408 through one or more error signals 420. As a result, under a conventional approach these errors cause the PCIE link to be re-established (e.g., reset). Exemplary aspects of the disclosure avoid a need for re-establishing the PCIE link (and any other disruptions) by incorporating circuitry (e.g., safe error circuitry or control circuitry) and/or software which consumes the error and reports to the originator, such as the host software 412, that no error occurred. In an exemplary aspect, the circuitry additionally provides safe (e.g., non-corrupted) data to the originator responsive to the operation request 416.

PCIE link errors can be considered correctable or uncorrectable. Correctable errors can impact performance (e.g., latency, bandwidth) of a PCIE link, but no data is lost and the PCIE link remains reliable. Correctable errors may generally be corrected by hardware. Uncorrectable errors, however, can result in lost information and/or impact the integrity of the PCIE link. Generally, uncorrectable errors cannot be corrected by PCIE hardware, and typically result in crashes of drivers and/or portions of operating systems in communication with the root complex 408. As a consequence, when an uncorrectable error is detected by the root complex 408, the PCIE link is generally terminated and re-established to prevent crashes and other disruptions from occurring. Exemplary aspects of the present disclosure provide for safe handling of uncorrectable errors to avoid a need for re-establishing the PCIE link.

In this regard, FIG. 4B is a block diagram of an exemplary PCIE uncorrectable error status register 422, illustrating various types of uncorrectable errors. In the computing system 400 of FIG. 4A, uncorrectable errors can be reported to the root complex 408 and/or the host software 412 through the PCIE uncorrectable error status register 422. In exemplary aspects, the PCIE uncorrectable error status register 422 may include various error statuses in accordance with the PCIE standard published by the PCI Special Interest Group (PCI-SIG). The PCIE uncorrectable error status register 422 may be an error status register associated with a PCIE link between a root complex device (e.g., host platform 402) and an endpoint device (e.g., device platform 404). These error statuses may include, but are not limited to, transaction layer packet (TLP) prefix blocked error status 424, atomic operation (AtomicOP) egress blocked status 426, multicast (MC) blocked TLP status 428, uncorrectable internal error status 430, access control service (ACS) violation status 432, unsupported request error status 434, end-to-end cyclic redundancy code (ECRC) error status 436, malformed TLP status 438, receiver overflow status 440, unexpected completion status 442, completer abort status 444, completion timeout status 446, flow control protocol error status 448, poisoned TLP status 450, surprise down error status 452, and data link protocol error status 454. When an uncorrectable error occurs, the PCIE hardware element 410 and/or device hardware 414 sets the corresponding error status bit 424, 426, 428, 430, 432, 434, 436, 438, 440, 442, 444, 446, 448, 450, 452, 454 in the PCIE uncorrectable error status register 422.

As an example, with reference to FIGS. 4A and 4B, the PCIE hardware element 410 may include the PCIE uncorrectable error status register 422. The PCIE hardware element 410 may receive an operation request 416, but the device hardware 414 experiences an uncorrectable internal error. As a result, the PCIE hardware element 410 and/or the device hardware 414 may set the bit in the PCIE uncorrectable error status register 422 corresponding to the uncorrectable internal error status 430. In response to the operation request 416, the uncorrectable internal error status 430 is reported to the root complex 408, and in some cases the PCIE uncorrectable error status register 422 may be forwarded to the root complex 408. The root complex 408 may store the uncorrectable internal error status 430 in a corresponding uncorrectable error status register in or associated with the root complex 408, where it is accessible by the host software 412 or other processes of the host platform 402.

Under a conventional approach, when the host software 412 (e.g., a driver or high level operating system) detects a set bit (such as the uncorrectable internal error status 430) in the PCIE uncorrectable error status register 422, it experiences a crash. The crash often results in the host software re-establishing the PCIE link, and may in some cases result in a restart of the entire computing system 400. The severity of a crash in the host software 412 can vary depending on the type of uncorrectable error which occurs (as indicated by the PCIE uncorrectable error status register 422). However, aspects of the present disclosure safely consume errors, such as uncorrectable errors, to avoid the need to go through re-establishment of the PCIE link and/or crashes in the host software 412. The errors are consumed by reporting to the host platform 402 (e.g., reporting to the host software 412) that no error has occurred (e.g., by ensuring that the PCIE uncorrectable error status register 422 accessed by the host software 412 is clear), as well as providing safe (e.g., non-corrupted) data to the host software 412 responsive to an operation request 416.

Safe error handling according to the present disclosure can be implemented through various approaches, such as depicted with respect to FIGS. 5-9 below. In a first non-limiting example depicted with respect to FIGS. 5 and 8, safe handling of link errors can be implemented on a host device (e.g., host platform 402), through control circuitry coupled to the root complex 408 and/or software, such as driver software for the PCIE link. In a second non-limiting example depicted with respect to FIGS. 6 and 8, safe handling of link errors can be implemented on a bridge between a host device (e.g., host platform 402) and an endpoint device (e.g., device platform 404), through control circuitry which can be semi-transparent to the host device. In a third non-limiting example depicted with respect to FIGS. 7 and 9, safe handling of link errors can be implemented on an endpoint device (e.g., a device platform 404), through control circuitry which monitors error conditions and consumes errors before they would be reported at the PCIE link.

FIG. 5 is a block diagram of the exemplary computing system 400 of FIG. 4A with the host platform 402 incorporating safe error circuitry 500 and/or software. In this regard, the safe error circuitry 500 (e.g., control circuitry configured to consume errors in the PCIE link) can be incorporated in the host platform 402, such as within or coupled to the root complex 408. When an error occurs in the PCIE link, the PCIE hardware element 410 in the device platform 404 (e.g., a PCIE endpoint) reports the error to the root complex 408 through one or more error signals 420. The error signals 420 may include the reporting of at least a portion of the PCIE uncorrectable error status register 422 in FIG. 4B. The safe error circuitry 500 is configured to consume, withhold, suppress, or otherwise conceal the error signals 420 from other portions of the host platform 402, such as the host software 412 (e.g., a driver or high level operating system). The safe error circuitry 500 consumes an error by 1) reporting to the originator of operation requests 416 for the device platform 404 (e.g., host software 412) that no error occurred, and 2) providing safe data to the originator when a response from the device platform 404 is expected.

Accordingly, when an error (such as an unrecoverable error) is received from the PCIE bus 406 (or read from a PCIE uncorrectable error status register in the device platform 404, such as the PCIE uncorrectable error status register 422 in FIG. 4B), the safe error circuitry 500 reports to the host software 412 that no error occurred. For example, the error may be stored in a PCIE uncorrectable error status register in the root complex 408. The host software 412 may at times (e.g., periodically or in connection with an operation request 416) request a report of the PCIE uncorrectable error status register (e.g., request the root complex 408 read the PCIE uncorrectable error status register). Notwithstanding one or more bits of the PCIE uncorrectable error status register indicating an error has occurred, the safe error circuitry 500 can cause the root complex 408 to report that no error has occurred. Under some circumstances, the device platform 404 may fail to respond to an operation request 416 within an allotted time (e.g., as defined in the PCIE specification or otherwise), causing the root complex 408 to assume that an error has occurred and set a bit in its PCIE uncorrectable error status register. In such cases, the safe error circuitry 500 can also consume the assumed error by causing the root complex 408 to report to the host software 412 that no error has occurred.

In some examples, the safe error circuitry 500 includes a completion generator 502. In this regard, the one or more error signals 420 can be received in response to or in connection with an operation request 416 sent by the root complex 408. Due to the error, the device platform 404 may fail to send data responsive to the operation request 416, or may send corrupted data to the root complex 408. Through the completion generator 502, when the safe error circuitry 500 consumes the error it also provides safe data to the host software 412 which is responsive to the operation request 416. The safe data generally is not an accurate response from the device platform 404 (since an accurate response has not been received), but it is data generated by the completion generator 502 which does not cause harm to the host software 412 or other processes of the host platform 402. For example, the safe data may include all zeros, all "F" values, or other non-corrupted data. Because the host software 412 receives some data in response to the operation request 416, the host software 412 may continue to operate without experiencing a crash or having a need to re-establish the PCIE link after not receiving expected data or after receiving corrupted data.

In some examples, the safe error circuitry 500 continues to consume the error so long as an error status exists (e.g., while the PCIE uncorrectable error status register has at least one bit set, or continuously or for a period of time after receiving an error signal 420). In some cases, the completion generator 502 may continue to reply to operation requests from the host software 412 while the safe error circuitry 500 prevents the root complex 408 from sending an operation request 416 over the PCIE bus 406. While the safe error circuitry 500 is consuming errors, the root complex 408 may attempt to correct the error or otherwise restore the PCIE link without re-establishing (e.g., resetting) the link. For example, the root complex 408 may allow additional time for the device platform 404 to complete operations and respond to the operation request 416 with successful data 418. As another example, the root complex 408 may re-enumerate the PCIE hardware element 410 to re-enable transactions with the device platform 404 after the error.

While the safe error circuitry 500 generally consumes and otherwise suppresses errors, the safe error circuitry 500 can also include an error monitor 504 which can monitor and/or store information about the consumed error. The host platform 402 may include special software 506, including a special register (e.g., a safe error status register), which can access the information from the error monitor 504. Through the special software 506 the host platform 402 can access information regarding the errors which are consumed by the safe error circuitry 500. For example, the error monitor 504 can set a bit in the safe error status register indicating the safe error circuitry 500 has consumed an error, or error information may be stored in the safe error status register. The error monitor 504 can monitor and/or store information such as the types of errors which have occurred, the time errors occur, the duration of errors, and/or the time a link is repaired. In some examples, the safe error circuitry 500 can alternatively or additionally include error information in the safe data provided by the completion generator 502.

FIG. 5 has been described generally with regard to handling errors through the safe error circuitry 500. It should be understood, however, that the functions of the safe error circuitry 500, including the completion generator 502 and the error monitor 504 can, in some aspects, be implemented through software or a combination of software and circuitry. For example, at least a portion of the functions described with respect to the safe error circuitry 500 may be performed through driver software in communication with or included in the root complex 408. In addition, the safe error circuitry 500 may be implemented instead through circuitry in other portions of the computing system 400, such as a bridge coupled to the PCIE bus 406 between the host platform 402 and the device platform 404.

In this regard, FIG. 6 is a block diagram of the exemplary computing system 400 of FIG. 4A with a bridge between the host platform 402 and the device platform 404 incorporating safe error circuitry 600. The safe error circuitry 600 can be or include a semi-transparent bridge 602 between the host platform 402 and the device platform 404, such that when no errors are present on the PCIE link, operation requests 416 sent by the host platform 402 (e.g., from the root complex 408) are forwarded through the semi-transparent bridge 602 to the device platform 404 (e.g., to the PCIE hardware element 410) with little or no interruption. Similarly, when the operation is successful, successful data 418 and/or a report indicating success sent by the PCIE hardware element 410 is forwarded through the semi-transparent bridge 602 to the root complex 408 with little or no interruption.

However, when an error occurs in the PCIE link, the safe error circuitry 600 intercepts the error signals 420 (which may be reported through a PCIE uncorrectable error status register, such as the uncorrectable error status register 422 in FIG. 4B) and consumes, withholds, suppresses, or otherwise conceals the error signals 420 from the host platform 402. Accordingly, when an error (such as an unrecoverable error) is received from the device platform 404 (or read from the PCIE uncorrectable error status register), the safe error circuitry 600 reports to the host platform 402 that no error occurred. Similar to the safe error circuitry 500 in FIG. 5, the safe error circuitry 600 consumes an error by 1) reporting to the host platform 402 that no error occurred, and 2) providing safe data to the host platform 402 when a response from the device platform 404 is expected. For example, the safe error circuitry 600 can send an indication of a clear uncorrectable error status register or otherwise report a successful operation in response to an operation request 416.

The semi-transparent bridge 602 generally includes a first bus interface which couples to the device platform 404 (e.g., a PCIE endpoint) through a PCIE bus coupled to the PCIE hardware element 410. The semi-transparent bridge 602 also includes a second bus interface which couples to the host platform 402 through a PCIE bus coupled to the root complex 408. The semi-transparent bridge 602 and/or the safe error circuitry 600 forwards or otherwise passes communications (including operation requests 416 and successful data 418) between the first bus interface and the second bus interface except when an error (e.g., an uncorrectable error) is detected over the first bus interface.

In this regard, the safe error circuitry 600 includes an error monitor 604, which monitors and/or stores reports of errors (e.g., uncorrectable errors) received from the PCIE hardware element 410 (e.g., by monitoring the first bus interface for errors). When an error is detected by the error monitor 604, a completion generator 606 consumes the error by generating a report to the host platform 402 that no error has occurred (e.g., by reporting to the second bus interface that no link error occurred). For example, the completion generator 606 may send an indication of a clear uncorrectable error status register to the root complex 408 (e.g., through the second bus interface). In some examples, the one or more error signals 420 are received in response to or in connection with an operation request 416 sent by the root complex 408. Due to the error, the device platform 404 may fail to send data responsive to the operation request 416, or may send corrupted data over the PCIE link. Through the completion generator 606, the safe error circuitry 600 can provide safe data to the host platform 402 which is responsive to the operation request 416 (e.g., by providing safe data to the second bus interface).

The safe data generally is not an accurate response from the device platform 404 (since an accurate response has not been received), but it is data generated by the completion generator 606 which does not cause harm to the processes of the host platform 402. This safe data is provided by the completion generator 606 to the root complex 408 as successful data 418, such that processes in the host platform 402 (e.g., the host software 412) may be unaware that an error has occurred, avoiding the host platform 402 experiencing a crash or a need for re-establishing the PCIE link after not receiving expected data or receiving corrupted data.

Under some circumstances, the device platform 404 may fail to respond to an operation request 416 within an allotted time, which may cause the root complex 408 to assume that an error has occurred. To avoid this error, the safe error circuitry 600 includes a completion timer 608 which monitors outgoing operation requests 416. When the allotted time has passed (which may be less than a completion time defined in the PCIE specification), the completion timer 608 causes the completion generator 606 to consume an assumed error by reporting to the root complex 408 that no error has occurred and providing safe data to the root complex 408 as successful data 418, avoiding the host platform 402 experiencing a crash or a need for re-establishing the PCIE link after not receiving expected data.

The safe error circuitry 600 may also include a link monitor 610 which monitors the PCIE link between the host platform 402 and the device platform 404 to detect link interruptions, linkdown, and other disruptions to the PCIE link, which may be considered to be PCIE link errors. In some cases, such disruptions in the PCIE link may be monitored between the safe error circuitry 600 and the device platform 404. When a disruption in the PCIE link is detected, the link monitor 610 causes the completion generator 606 to consume any reported or assumed error by reporting to the root complex 408 that no error has occurred and providing safe data to the root complex 408 as successful data 418.

In some examples, the safe error circuitry 600 continues to consume any detected or assumed error so long as an error status exists (e.g., while the PCIE uncorrectable error status register has at least one bit set, continuously or for a period of time after receiving an error signal 420, or after the completion timer 608 or the link monitor 610 determine an error has occurred). In some cases, the completion generator 606 may continue to reply to operation requests 416 from the host platform 402 while the safe error circuitry 600 blocks (and optionally stores) any additional operation requests 416 from being sent to the PCIE hardware element 410. While the safe error circuitry 600 is consuming errors, the safe error circuitry 600 may attempt to correct the error or otherwise restore the PCIE link without re-establishing (e.g., resetting) the link. For example, the safe error circuitry 600 may allow additional time for the device platform 404 to complete operations and respond to the operation request 416 with successful data 418. As another example, the safe error circuitry 600 may re-enumerate the PCIE hardware element 410 (or cause the root complex 408 to re-enumerate the PCIE hardware element 410) to re-enable transactions with the device platform 404 after the error.

While the safe error circuitry 600 generally consumes and otherwise suppresses errors, the safe error circuitry 600 can also store and/or transmit information about the consumed error. For example, the safe data provided by the completion generator 606 can indicate an error has occurred and/or include information about the error. As another example, the safe error circuitry 600 can transmit a safe error status signal and/or an indication of a safe error status register to the host platform 402. The safe error circuitry 600 can store and/or transmit information (e.g., in the safe data, in the safe error status signal) such as the types of errors which have occurred, the time errors occur, the duration of errors, and/or the time a link is repaired.

FIG. 7 is a block diagram of the exemplary computing system of FIG. 4A with the device platform 404 incorporating safe error circuitry 700. The safe error circuitry 700 can be incorporated in or coupled to the device hardware 414 and/or the PCIE hardware element 410, and can monitor the device hardware 414 and/or the PCIE hardware element 410 to detect when an error occurs, and consumes, withholds, suppresses, or otherwise conceals reporting error conditions from the host platform 402. Similar to the safe error circuitry 600 in FIG. 6, the safe error circuitry 700 consumes an error by 1) reporting to the host platform 402 that no error occurred, and 2) providing safe data to host platform 402 when a response from the device platform 404 is expected.

In this regard, the safe error circuitry 700 includes an error monitor 702, which monitors the device hardware 414, the PCIE hardware element 410, and/or error reports for error conditions. In a first aspect, the error monitor 702 monitors the device hardware 414 for error conditions, such as uncorrectable internal errors or other failures in the device hardware 414. In another aspect, the error monitor 702 monitors the PCIE hardware element 410 for link interruptions, linkdown, and other disruptions to the PCIE link between the PCIE hardware element 410 and the root complex 408. In another aspect, the error monitor 702 monitors reports of errors, such as through monitoring a PCIE uncorrectable error status register (e.g., the PCIE uncorrectable error status register 422 in FIG. 4B) in the device platform 404.

When an error is detected by the error monitor 702, a completion generator 704 consumes the error by generating a report to the host platform 402 that no error has occurred. For example, the completion generator 704 may cause the PCIE hardware element 410 to send an indication of a clear uncorrectable error status register to the root complex 408. In some examples, the error conditions are detected in response to or in connection with an operation request 416 received from the host platform 402. The completion generator 704 may intercept any potentially corrupted data from the device hardware 414, and instead respond to the operation request 416 with a fake success 706, which includes providing safe data to the host platform 402 which is responsive to the operation request 416.

The safe data generally is not an accurate response from the device platform 404, (since any response generated by the device hardware 414 is assumed to be corrupted), but it is data generated by the completion generator 704 which does not cause harm to the processes of the host platform 402. This safe data is provided by the completion generator 704 to the PCIE hardware element 410 as a fake success 706, and sent to the host platform 402 as successful data 418, such that processes in the host platform 402 (e.g., the host software 412) may be unaware that an error has occurred, avoiding the host platform 402 experiencing a crash or a need for re-establishing the PCIE link after not receiving expected data or receiving corrupted data.

Under some circumstances, the device hardware 414 may fail to respond to an operation request 416 within an allotted time, and if the device platform 404 fails to send a response the root complex 408 would assume that an error has occurred. To avoid this error, the safe error circuitry 700 includes a completion timer 708 which monitors incoming operation requests 416 received at the PCIE hardware element 410. When the allotted time has passed (which may be less than a completion time defined in the PCIE specification), the completion timer 708 causes the completion generator 704 to consume an assumed error by reporting a fake success 706 to the PCIE hardware element 410 and providing safe data to be sent by the PCIE hardware element 410 as successful data 418, avoiding the host platform 402 experiencing a crash or a need for re-establishing the PCIE link after not receiving expected data.

In some examples, the safe error circuitry 700 continues to consume any detected or assumed error so long as an error status exists (e.g., while the PCIE uncorrectable error status register has at least one bit set, continuously or for a period of time after the error monitor 702 determines an error condition exists, or after the completion timer 708 determines an error has occurred). In some cases, the completion generator 704 may continue to reply to operation requests 416 from the host platform 402 while the safe error circuitry 700 blocks (and optionally stores) any additional operation requests 416 received from the host platform 402 from being processed by the device hardware 414. While the safe error circuitry 700 is consuming errors, the safe error circuitry 700 may attempt to correct the error or otherwise restore the PCIE link without re-establishing (e.g., resetting) the link. For example, the safe error circuitry 700 may allow additional time for the device platform 404 to complete operations and respond to the operation request 416 with successful data 418. As another example, the safe error circuitry 700 may reset the device hardware 414 and/or other logic elements behind the PCIE hardware element 410, including buses, to re-enable transactions with the host platform 402 after the error.

While the safe error circuitry 700 generally consumes and otherwise suppresses errors, the safe error circuitry 700 can also store and/or transmit information about the consumed error. For example, the safe data provided by the completion generator 704 can indicate an error has occurred and/or include information about the error. The safe error circuitry 700 can store and/or transmit information such as the types of errors which have occurred, the time errors occur, the duration of errors, and/or the time a link is repaired. With reference to FIGS. 2 and 7, the device platform 404 may include the configuration registers 214, the capability registers 216, and/or the extended configuration register space 218. In some cases, one or more of these registers 214, 216, 218 may indicate the device platform 404 includes the safe error circuitry 700.

Figure 8:
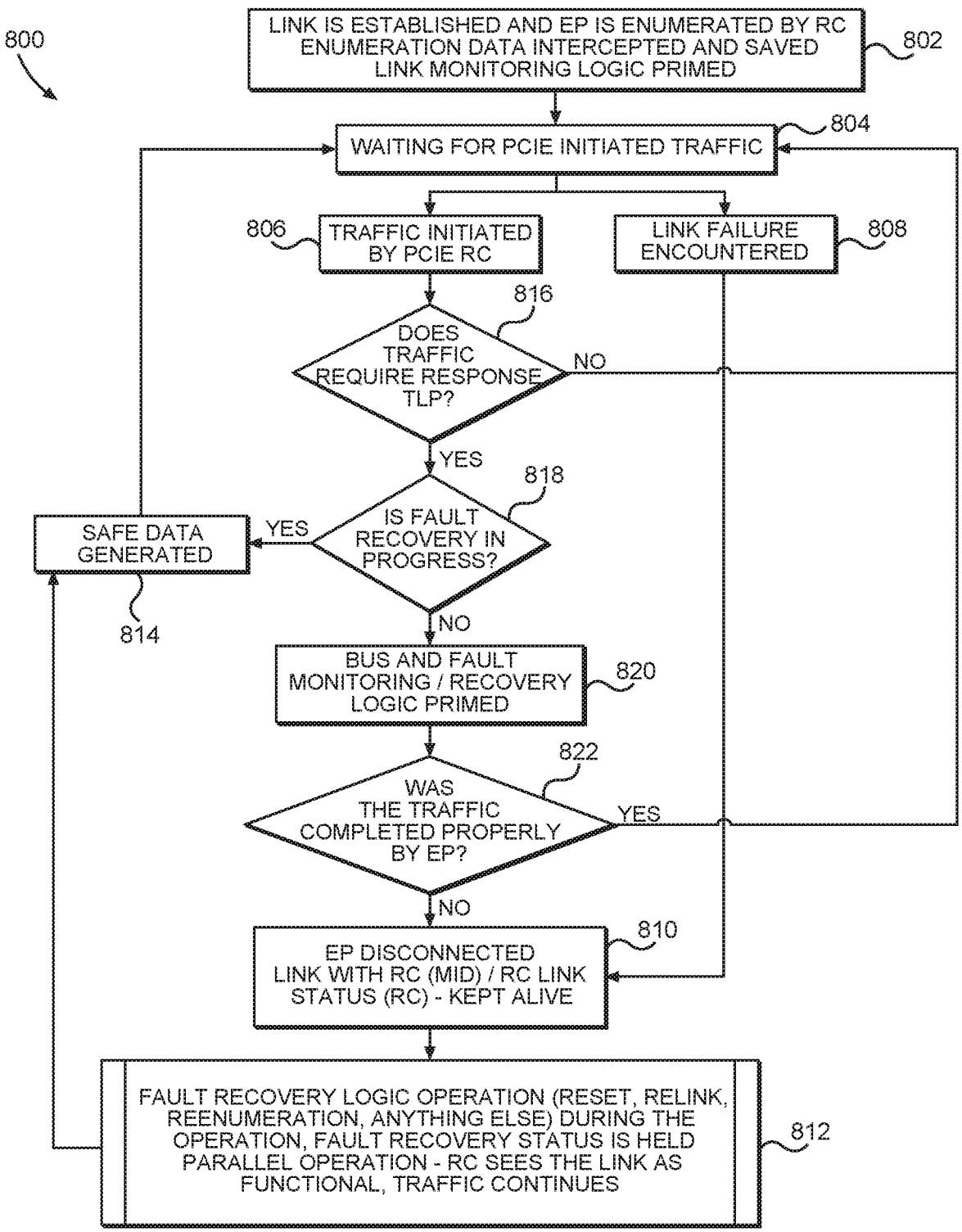
FIG. 8 is a flowchart illustrating an exemplary process for safe handling of link errors in the PCIE computing system depicted in FIGS. 4A-6.

The safe error circuitry 500, 600 depicted in FIGS. 5 and 6 can be configured to consume, withhold, suppress, or otherwise conceal error signals 420 and conditions from the host platform 402 (or the host software 412 within the host platform 402) based on a process. FIG. 8 is a flowchart illustrating an exemplary process 800 for safe handling of link errors in the PCIE computing system 400 depicted in FIGS. 4A-6.

With reference to FIG. 8, a link is established between the host platform 402 and the device platform 404, and the endpoint (e.g., the PCIE hardware element 410) is enumerated by the root complex 408. The safe error circuitry 500, 600 intercepts and saves enumeration data, and link monitoring logic (e.g., the error monitor 504, the completion generator 502, the error monitor 604, the completion timer 608, the link monitor 610) is primed (block 802). The safe error circuitry 500, 600 then waits for PCIE-initiated traffic (block 804). The safe error circuitry 500, 600 may then detect traffic (e.g., an operation request 416) initiated by the PCIE root complex 408 (block 806) or it may encounter a link failure (block 808). The link failure (block 808) may be detected by an error monitor 504, completion generator 502, error monitor 604, and/or a link monitor 610, such as through receiving one or more error signals 420 or reading a PCIE uncorrectable error status register 422. When the link failure is detected, the endpoint (e.g., device platform 404 or PCIE hardware element 410) is disconnected (block 810). In the case where the safe error circuitry 500 is implemented in the root complex 408, the link status at the root complex 408 is kept alive. In the case where the safe error circuitry 600 is implemented in a bridge between the root complex 408 and the PCIE hardware element 410, the link between the safe error circuitry 600 and the root complex 408 is kept alive.

Once the safe error circuitry 500, 600 disconnects the endpoint (e.g., device platform 404 or PCIE hardware element 410), fault recovery logic in the safe error circuitry 500, 600 operates to reset, re-link, re-enumerate, or otherwise attempt to correct the link error (block 812). During the operation of the fault recovery logic, fault recovery status is held. In the case where the safe error circuitry 600 is implemented in a bridge between the root complex 408 and the PCIE hardware element 410, the root complex 408 sees the link as functional and continues traffic. The safe error circuitry 500, 600 then generates safe data responsive to any operation requests 416 from the host platform 402 (e.g., by the host software 412 or the root complex 408) (block 814) and returns to wait for PCIE-initiated traffic (block 804).

Alternatively, after the safe error circuitry 500, 600 waits for PCIE-initiated traffic (block 804), the safe error circuitry 500, 600 may then detect traffic (e.g., operation request 416) initiated by the PCIE root complex 408 (block 806). The safe error circuitry 500, 600 then determines whether the detected traffic (e.g., operation request 416) requires a response TLP or other type of response (block 816). If no response is required, the safe error circuitry 500, 600 returns to wait for PCIE-initiated traffic (block 804). If a response is required, the safe error circuitry 500, 600 determines whether fault recovery is in progress (block 818). If fault recovery is in progress, the safe error circuitry 500, 600 then generates safe data responsive to the operation request 416 (e.g., traffic initiated by the PCIE root complex 408) (block 814) and returns to wait for PCIE-initiated traffic (block 804).

Alternatively, if fault recovery is not in progress, bus and fault monitoring logic (e.g., the error monitor 504, the completion generator 502, the error monitor 604, the completion timer 608, the link monitor 610) and recovery logic is primed (block 820). The safe error circuitry 500, 600 then determines whether the traffic (e.g., operation request 416) was properly completed by the endpoint (e.g., device platform 404 or PCIE hardware element 410) (block 822). If the traffic was properly completed by the endpoint, the safe error circuitry 500, 600 then returns to wait for PCIE-initiated traffic (block 804). If the traffic was not properly completed by the endpoint, the endpoint is disconnected and the link status at the root complex 408 or the link between the safe error circuitry 600 and the root complex 408 is kept alive (block 810). Then fault recovery logic in the safe error circuitry 500, 600 operates to reset, re-link, re-enumerate, or otherwise attempt to correct the link error (block 812). During the operation of the fault recovery logic, fault recovery status is held. The root complex 408 sees the link as functional and continues traffic. The safe error circuitry 500, 600 then generates safe data responsive to the operation request 416 (block 814) and returns to wait for PCIE-initiated traffic (block 804).

The safe error circuitry 700 depicted in FIG. 7 can be configured to consume, withhold, suppress, or otherwise conceal error conditions from the host platform 402 based on a process. FIG. 9 is a flowchart illustrating an exemplary process for safe handling of link errors in the PCIE computing system depicted in FIGS. 4A, 4B, and 7. The safe error circuitry 700 waits for PCIE-initiated traffic (block 902). The safe error circuitry 700 may then detect traffic (e.g., an operation request 416) initiated by the PCIE root complex 408 and received by the endpoint (e.g., device platform 404 or PCIE hardware element 410) (block 904). The safe error circuitry 700 then determines whether the detected traffic (e.g., operation request 416) requires a response TLP or other type of response (block 906). If no response is required, the safe error circuitry 700 returns to wait for PCIE-initiated traffic (block 902). If a response is required, the safe error circuitry 700 determines whether fault recovery is in progress (block 908). If fault recovery logic is in progress, the safe error circuitry 700 then generates safe data responsive to the operation request 416 (e.g., traffic initiated by the PCIE root complex 408) (block 910) and returns to wait for PCIE-initiated traffic (block 902).

Alternatively, if fault recovery is not in progress, bus and fault monitoring logic (e.g., the error monitor 702, the completion timer 708) and recovery logic is primed (block 912). The safe error circuitry 700 then determines whether the traffic (e.g., operation request 416) was properly completed (e.g., by the device hardware 414) (block 914). If the traffic was properly completed, the safe error circuitry 700 then returns to wait for PCIE-initiated traffic (block 902). If the traffic was not properly completed by the endpoint, the internal buses (e.g., in the device hardware 414) of the device platform 404 are disconnected (block 916). Then fault recovery logic in the safe error circuitry 700 operates to attempt to correct the error or otherwise restore the PCIE link without re-establishing (e.g., resetting) the link (block 918). For example, the safe error circuitry 700 may allow additional time for the device platform 404 to complete operations and respond to the operation request 416. As another example, the safe error circuitry 700 may reset the device hardware 414 and/or other logic elements behind the PCIE hardware element 410, including buses, to re-enable transactions with the host platform 402 after the error. During the operation of the fault recovery logic, fault recovery status is held. Traffic continues to be received by the PCIE hardware element 410. Concurrently with the operation of the fault recovery logic (block 916), the safe error circuitry 700 generates safe data responsive to the operation request 416 (block 910) and returns to wait for PCIE-initiated traffic (block 902).

The safe handling of link errors in a PCIE device according to aspects disclosed herein may be provided in or integrated into any processor-based device. Examples, without limitation, include a set top box, an entertainment unit, a navigation device, a communications device, a fixed location data unit, a mobile location data unit, a global positioning system (GPS) device, a mobile phone, a cellular phone, a smart phone, a session initiation protocol (SIP) phone, a tablet, a phablet, a server, a computer, a portable computer, a mobile computing device, a wearable computing device (e.g., a smart watch, a health or fitness tracker, eyewear, etc.), a desktop computer, a personal digital assistant (PDA), a monitor, a computer monitor, a television, a tuner, a radio, a satellite radio, a music player, a digital music player, a portable music player, a digital video player, a video player, a digital video disc (DVD) player, a portable digital video player, an automobile, a vehicle component, avionics systems, a drone, and a multicopter.

In this regard, FIG. 10 is a block diagram of an exemplary processor-based system that can include the computing system 400 of FIGS. 1-9. The computing system 1000 includes an application processor 1004 (e.g., application processor 302 in FIG. 3, sometimes referred to as a host) that communicates with a mass storage element 1006 through a universal flash storage (UFS) bus 1008. The application processor 1004 may further be connected to a display 1010 through a display serial interface (DSI) bus 1012 and a camera 1014 through a camera serial interface (CSI) bus 1016. Various audio elements such as a microphone 1018, a speaker 1020, and an audio codec 1022 may be coupled to the application processor 1004 through a serial low-power interchip multimedia bus (SLIMbus) 1024. Additionally, the audio elements may communicate with each other through a SOUNDWIRE bus 1026. A modem 1028 may also be coupled to the SLIMbus 1024 and/or the SOUNDWIRE bus 1026. The modem 1028 may further be connected to the application processor 1004 through a PCI or PCIE bus 1030 and/or a system power management interface (SPMI) bus 1032.

With continued reference to FIG. 10, the SPMI bus 1032 may also be coupled to a local area network (LAN or WLAN) IC (LAN IC or WLAN IC) 1034, a power management integrated circuit (PMIC) 1036, a companion IC (sometimes referred to as a bridge chip) 1038, and a radio frequency IC (RFIC) 1040. It should be appreciated that separate PCI buses 1042 and 1044 may also couple the application processor 1004 to the companion IC 1038 and the WLAN IC 1034. The application processor 1004 may further be connected to sensors 1046 through a sensor bus 1048. The modem 1028 and the RFIC 1040 may communicate using a bus 1050.

With continued reference to FIG. 10, the RFIC 1040 may couple to one or more radio frequency front end (RFFE) elements, such as an antenna tuner 1052, a switch 1054, and a power amplifier 1056 through an RFFE bus 1058. Additionally, the RFIC 1040 may couple to an envelope tracking power supply (ETPS) 1060 through a bus 1062, and the ETPS 1060 may communicate with the power amplifier 1056. Collectively, the RFFE elements, including the RFIC 1040, may be considered an RFFE system 1064. It should be appreciated that the RFFE bus 1058 may be formed from a clock line and a data line (not illustrated).

Those of skill in the art will further appreciate that the various illustrative logical blocks, modules, circuits, and algorithms described in connection with the aspects disclosed herein may be implemented as electronic hardware, instructions stored in memory or in another computer readable medium and executed by a processor or other processing device, or combinations of both. The devices described herein may be employed in any circuit, hardware component, integrated circuit (IC), or IC chip, as examples. Memory disclosed herein may be any type and size of memory and may be configured to store any type of information desired. To clearly illustrate this interchangeability, various illustrative components, blocks, modules, circuits, and steps have been described above generally in terms of their functionality. How such functionality is implemented depends upon the particular application, design choices, and/or design constraints imposed on the overall system. Skilled artisans may implement the described functionality in varying ways for each particular application, but such implementation decisions should not be interpreted as causing a departure from the scope of the present disclosure.

The various illustrative logical blocks, modules, and circuits described in connection with the aspects disclosed herein may be implemented or performed with a processor, a Digital Signal Processor (DSP), an Application Specific Integrated Circuit (ASIC), a Field Programmable Gate Array (FPGA) or other programmable logic device, discrete gate or transistor logic, discrete hardware components, or any combination thereof designed to perform the functions described herein. A processor may be a microprocessor, but in the alternative, the processor may be any conventional processor, controller, microcontroller, or state machine. A processor may also be implemented as a combination of computing devices (e.g., a combination of a DSP and a microprocessor, a plurality of microprocessors, one or more microprocessors in conjunction with a DSP core, or any other such configuration).

The aspects disclosed herein may be embodied in hardware and in instructions that are stored in hardware, and may reside, for example, in Random Access Memory (RAM), flash memory, Read Only Memory (ROM), Electrically Programmable ROM (EPROM), Electrically Erasable Programmable ROM (EEPROM), registers, a hard disk, a removable disk, a CD-ROM, or any other form of computer readable medium known in the art. An exemplary storage medium is coupled to the processor such that the processor can read information from, and write information to, the storage medium. In the alternative, the storage medium may be integral to the processor. The processor and the storage medium may reside in an ASIC. The ASIC may reside in a remote station. In the alternative, the processor and the storage medium may reside as discrete components in a remote station, base station, or server.

It is also noted that the operational steps described in any of the exemplary aspects herein are described to provide examples and discussion. The operations described may be performed in numerous different sequences other than the illustrated sequences. Furthermore, operations described in a single operational step may actually be performed in a number of different steps. Additionally, one or more operational steps discussed in the exemplary aspects may be combined. It is to be understood that the operational steps illustrated in the flowchart diagrams may be subject to numerous different modifications as will be readily apparent to one of skill in the art. Those of skill in the art will also understand that information and signals may be represented using any of a variety of different technologies and techniques. For example, data, instructions, commands, information, signals, bits, symbols, and chips that may be referenced throughout the above description may be represented by voltages, currents, electromagnetic waves, magnetic fields or particles, optical fields or particles, or any combination thereof.

The previous description of the disclosure is provided to enable any person skilled in the art to make or use the disclosure. Various modifications to the disclosure will be readily apparent to those skilled in the art, and the generic principles defined herein may be applied to other variations without departing from the spirit or scope of the disclosure. Thus, the disclosure is not intended to be limited to the examples and designs described herein, but is to be accorded the widest scope consistent with the principles and novel features disclosed herein.

What is claimed is:

1. A Peripheral Component Interconnect (PCI) express (PCIE) root complex device, comprising:
   a bus interface configured to be coupled to a PCIE endpoint; and
   control circuitry configured to:
      establish a PCIE link between the PCIE root complex device and the PCIE endpoint over the bus interface;
      send an operation request to the PCIE endpoint through the PCIE link;
      detect an error in the PCIE link; and
      consume the error to avoid re-establishing the PCIE link by:
         reporting to a host of the PCIE root complex device that no error occurred; and
         providing safe data to the host in response to the operation request.

2. The PCIE root complex device of claim 1, wherein the error in the PCIE link is an uncorrectable error.

3. The PCIE root complex device of claim 1, wherein the control circuitry is configured to detect the error in the PCIE link by reading an error status register associated with the PCIE link.

4. The PCIE root complex device of claim 3, wherein the control circuitry is further configured to:
   receive a request by the host to read the error status register; and
   consume the error by reporting to the host that the error status register indicates no error occurred.

5. The PCIE root complex device of claim 3, further comprising a safe error status register accessible to the host; wherein the control circuitry is further configured to consume the error by setting at least one bit of the safe error status register.

6. The PCIE root complex device of claim 5, wherein the control circuitry is further configured to consume the error by providing error information in the safe error status register.

7. The PCIE root complex device of claim 3, wherein the control circuitry is configured to detect the error in the PCIE link without receiving data from the PCIE endpoint responsive to the operation request.

8. The PCIE root complex device of claim 1, wherein the safe data provided to the host comprises error information.

9. The PCIE root complex device of claim 1, wherein the control circuitry is further configured to consume the error by attempting to correct the error in the PCIE link while reporting to the host that no error occurred.

10. The PCIE root complex device of claim 1 integrated into an integrated circuit (IC).

11. The PCIE root complex device of claim 1 integrated into a device selected from the group consisting of: a set top box; an entertainment unit; a navigation device; a communications device; a fixed location data unit; a mobile location data unit; a global positioning system (GPS) device; a mobile phone; a cellular phone; a smart phone; a session initiation protocol (SIP) phone; a tablet; a phablet; a server; a computer; a portable computer; a mobile computing device; a wearable computing device; a desktop computer; a personal digital assistant (PDA); a monitor; a computer monitor; a television; a tuner; a radio; a satellite radio; a music player; a digital music player; a portable music player; a digital video player; a video player; a digital video disc (DVD) player; a portable digital video player; an automobile; a vehicle component; avionics systems; a drone; and a multicopter.

12. A semi-transparent bridge for a Peripheral Component Interconnect (PCI) express (PCIE) link, comprising:
   a first bus interface configured to couple to a PCIE endpoint;
   a second bus interface configured to couple to a PCIE root complex; and
   control circuitry configured to:
      forward an operation request from the second bus interface to the first bus interface;
      monitor the first bus interface for a link error; and
      consume the link error by:
         reporting to the second bus interface that no link error occurred; and
         providing safe data to the second bus interface in response to the operation request.

13. The semi-transparent bridge of claim 12, wherein the control circuitry is further configured to pass communications between the first bus interface and the second bus interface except when the link error is an uncorrectable error.

14. The semi-transparent bridge of claim 12, wherein the control circuitry is configured to monitor the first bus interface for the link error by monitoring an error status received on the first bus interface.

15. The semi-transparent bridge of claim 14, wherein the reporting to the second bus interface that no link error occurred comprises providing data to an error status register of the PCIE root complex which does not include an indication of the link error.

16. The semi-transparent bridge of claim 15, wherein the control circuitry is further configured to consume the link error by transmitting a safe error status signal over the second bus interface, the safe error status signal indicating to the PCIE root complex that the link error was consumed.

17. The semi-transparent bridge of claim 14, wherein the control circuitry is configured to detect the link error without receiving data from the PCIE endpoint responsive to the operation request.

18. The semi-transparent bridge of claim 12, wherein the control circuitry is further configured to consume the link error by attempting to correct the link error while reporting to the second bus interface that no link error occurred.

19. A method comprising:
  establishing a Peripheral Component Interconnect (PCI) express (PCIE) link between an originator and an endpoint;
  receiving an operation request from the originator to the endpoint;
  detecting an error in the PCIE link; and
  consuming the error to avoid re-establishing the PCIE link, comprising:
    reporting to the originator that no error occurred; and
    providing safe data to the originator in response to the operation request.

20. The method of claim 19, wherein the detecting the error in the PCIE link comprises detecting data in an uncorrectable error status register.

21. The method of claim 20, wherein the consuming the error further comprises reporting to the originator that the uncorrectable error status register indicates no error occurred.

22. The method of claim 19, wherein the safe data provided to the originator in response to the operation request comprises an indication of the error in the PCIE link.

23. The method of claim 19, wherein the detecting the error in the PCIE link comprises not receiving data from the endpoint responsive to the operation request within an allotted time.

24. The method of claim 23, wherein the consuming the error further comprises:
  receiving the data responsive to the operation request after the providing the safe data to the originator; and
  providing the data responsive to the operation request to the originator.

25. The method of claim 19, wherein the consuming the error further comprises attempting to correct the error in the PCIE link while reporting to the originator that no error occurred.

26. A system comprising:
  a Peripheral Component Interconnect (PCI) express (PCIE) root complex device, comprising:
    a first PCIE bus interface to be coupled to a PCIE link; and
    first control circuitry configured to send an operation request over the PCIE link via the first PCIE bus interface;
  a PCIE endpoint device, comprising:
    a second PCIE bus interface to be coupled to the PCIE link; and
    second control circuitry configured to receive the operation request via the second PCIE bus interface and process the operation request; and
  safe error circuitry configured to:
    detect an error in the PCIE link; and
    consume the error by:
      reporting to a host in the PCIE root complex device that no error occurred in the PCIE link; and
      providing safe data to the host in response to the operation request.

27. The system of claim 26, wherein:
  the first control circuitry comprises the safe error circuitry; and
  the safe error circuitry is further configured to:
    receive a request by the host to read an error status register; and
    consume the error by reporting to the host that the error status register indicates no error occurred.

28. The system of claim 26, wherein:
  the second control circuitry comprises the safe error circuitry; and
  the safe error circuitry is further configured to detect the error in the PCIE link by detecting a lack of response at an internal bus of the PCIE endpoint device within an allotted time.

29. The system of claim 26, further comprising a semi-transparent bridge coupled between the first PCIE bus interface and the second PCIE bus interface;
  wherein the semi-transparent bridge comprises the safe error circuitry.

30. The system of claim 29, wherein the semi-transparent bridge is configured to pass communications between the PCIE root complex device and the PCIE endpoint device except when the error in the PCIE link is an uncorrectable error.

* * * * *